United States Patent [19]

Kruger

[11] 4,436,095

[45] Mar. 13, 1984

[54] METHOD AND APPARATUS FOR IMAGING A BODY

[75] Inventor: Robert A. Kruger, Salt Lake City, Utah

[73] Assignee: Thomson-CSF Broadcast, Inc., Stamford, Conn.

[21] Appl. No.: 333,558

[22] Filed: Dec. 22, 1981

[51] Int. Cl.³ ............................................. A61B 6/00
[52] U.S. Cl. .................................................. 128/654
[58] Field of Search ............................. 128/653-654; 358/111

[56] References Cited

U.S. PATENT DOCUMENTS

| | | | |
|---|---|---|---|
| 4,037,585 | 7/1977 | Gildenberg | 128/654 |
| 4,101,961 | 7/1978 | Reiber | 364/417 |
| 4,246,607 | 1/1981 | Vijverberg | 128/653 X |
| 4,249,825 | 2/1981 | Shapiro | 128/654 X |
| 4,263,916 | 4/1981 | Brooks et al. | 128/654 |
| 4,323,973 | 4/1982 | Greenfield | 358/111 X |
| 4,335,427 | 6/1982 | Hunt et al. | 358/111 X |
| 4,367,490 | 1/1983 | Riederer | 358/111 X |

OTHER PUBLICATIONS

Tebby, A. J., "Modifying the Contrast of an Image", UK Patent Application GB2061660A Published 13 May 1981.
Kruger, R. A. et al., "A Digital Video Image Processor for Real-Time Subtraction X-Ray Imaging", Optical Engineering, vol. 17, No. 6, Nov.-Dec. 1978.
Mistretta et al., U.K. Patent Application GB2020945A, published 21 Nov. 1979.

Primary Examiner—Kyle L. Howell
Assistant Examiner—Francis J. Jaworski
Attorney, Agent, or Firm—Martin Novack

[57] ABSTRACT

An improved method and apparatus for generating video images of the internal structure of a body is disclosed. A contrast medium is injected into the vessel to be imaged. Radiation is directed at the body, and radiation which passes through the body is detected and converted into a series of frames of electronic video signals, preferably in digital form. The frames represent images of the radiation transmission characteristics of the body at a series of successive times. Each frame includes an array of pixels, the video level at each pixel of a frame being determined by the radiation transmissivity of the body through an elemental region thereof. An initial video frame, i.e., the first video frame generated after the initiation of video processing, is stored in a digital video frame store. The video signal level at each pixel of the next frame is compared to the video signal level of the corresponding pixel of the stored frame. The lower of the two video signal levels being compared is selected and said selected video signal level is re-stored (in place of the previously stored value) at the particular pixel in the video frame store. This is done for each pixel of the frame. The process is then repeated for subsequent frames. In this manner, the stored video frame is dynamically processed to retain, at each pixel, a video signal level that represents the highest opacity to radiation during the video processing period through the elemental region of the body that corresponds geometrically to the particular pixel.

12 Claims, 3 Drawing Figures

METHOD AND APPARATUS FOR IMAGING A BODY

BACKGROUND OF THE INVENTION

This invention relates to techniques for obtaining radiographic images and, more particularly, to an apparatus and method for obtaining improved radiographic images of opacified anatomy using a fluoroscopic type of equipment in conjunction with a video processor.

A typical x-ray fluoroscopy apparatus includes an x-ray source and an image intensifier which is used to detect the x-radiation. The output of the image intensifier is viewed by a television camera, and the resultant television signal can be presented on a monitor and/or recorded. When a body, such as that of a patient, is interposed between the x-ray source and the detector, x-rays are absorbed in varying degrees depending upon the thickness and composition of different regions of the body. This results in the presentation of a two-dimensional image that can be used, for example, for diagnosing structural abnormalities within the body.

The ability to "see" structure in the body using the described technique depends on the x-ray absorption properties of the structure of interest in relation to the x-ray absorption properties of the material(s) adjacent to the structure. The greater the difference, the greater the "contrast" the structure of interest will have in the resulting television image. The greater the contrast, the greater the clarity of the structure in the image. Consequently, achieving high contrast is a desirable quality with this imaging procedure.

Radiographic contrast agents are used to create a large difference in x-ray absorption behavior where little or none previously existed. For example, blood vessels are virtually invisible on fluoroscopic images (except in the chest) because blood, muscle, fat and soft tissue all possess similar x-ray absorption behavior. Radiographic contrast agents contain material (e.g. air, barium, iodine) which has x-ray absorption properties dissimilar to blood, muscle, fat and the soft tissue. For example, when a bolus of iodinated liquid contrast material is injected into an artery or vein, the vascular structure is given artificially higher contrast on an x-ray image while the contrast material is present within a certain vascular segment. The contrast agent, flowing along with the blood, rapidly washes out of one segment and moves on to the next. In order to outline large segments of vasculature, large boluses of long duration (several second) usually are administered. Since iodinated contrast agents are toxic and present small but significant patient discomfort, as well as some risk of serious complications, only limited quantities are used in common procedures.

It is among the objects of this invention to reduce the amount of contrast material needed for a given procedure, and/or to enhance the image that can be obtained when using a given amount of contrast material. It is a further object hereof to generate improved images of the internal structure of a body.

SUMMARY OF THE INVENTION

The present invention is directed to an improved method and apparatus for generating video images of the internal structure of a body. In accordance with the method of the invention, a contrast medium is injected into the body, typically into the vessel to be imaged or leading into the vessel to be imaged. (As used herein "vessel" is intended to mean any one or plurality of fluid-carrying ducts or tubes; particularly, but not limited to, the vascular system.) A source of radiation, typically x-rays, is directed at the body, and radiation which passes through the body is detected and converted into a series of frames of electronic video signals, preferably in digital form. The frames represent images of the radiation transmission characteristics of the body at a series of successive times. Each frame includes an array of pixels, the video level at each pixel of a frame being determined by the radiation transmissivity of the body through an elemental region thereof. An initial video frame, i.e., the first video frame generated after the initiation of video processing, is stored in a digital video frame store. The video signal level at each pixel of the next frame is compared to the video signal level of the corresponding pixel of the stored frame. The lower of the two video signal levels being compared is selected and said selected video signal level is re-stored (in place of the previously stored value) at the particular pixel in the video frame store. This is done for each pixel of the frame. The process is then repeated for the next video frame, the video signal level at each pixel thereof being compared against the corresponding pixel of the latest re-stored frame, with the lower video signal level again being re-stored at the particular pixel. In this manner, the stored video frame is dynamically processed to retain, at each pixel, a video signal level that represents the highest opacity to radiation during the video processing period through the elemental region of the body that corresponds geometrically to the particular pixel.

With the technique hereof, one can obtain, using a relatively short duration bolus, a processed image that is comparable to the image otainable using a relatively long duration bolus.

Further features and advantages of the invention will become more readily apparent from the following detailed description when taken in conjunction with the accompanying drawings.

DESCRIPTION OF THE PREFERRED EMBODIMENT

Figure 1:
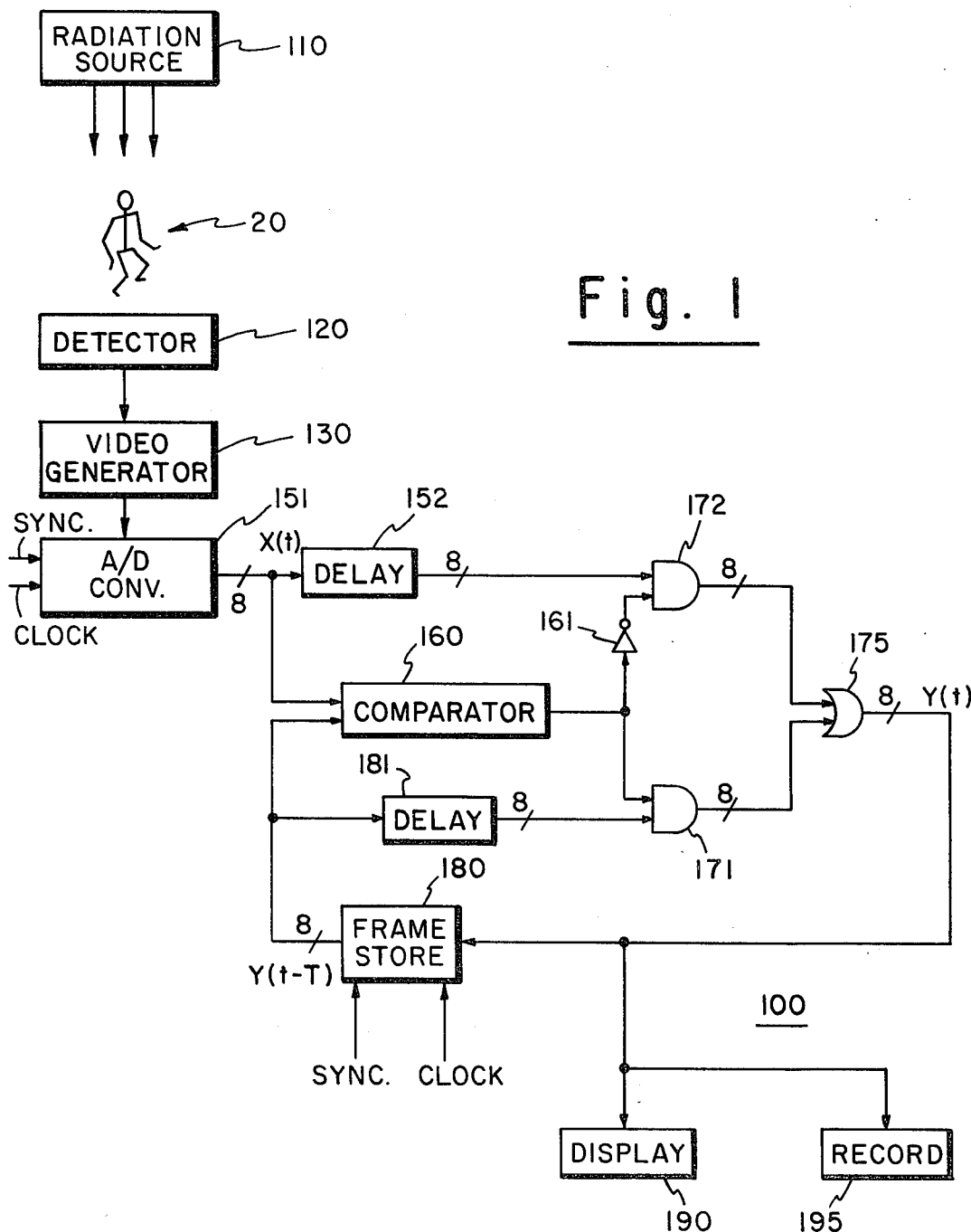
FIG. 1 is a block diagram of an apparatus in accordance with the invention and which can be used in practicing the method of the invention.

Referring to FIG. 1, there is shown a block diagram of an apparatus 100 for obtaining a displayed image of the internal structure of a body 20. The apparatus 100 conventionally includes a radiation source 110, typically an x-ray source, a detector 120, and a video generator 130. The combination of detector and video generator may include, for example, an x-ray image intensifier in conjunction with a television camera. The output of video generator 130 is coupled to an analog-to-digital converter 151 which converts the television signal into digital form. Equipment for obtaining the digitized television signal is well known in the art and commercially available, an example being the model AD-964310 manufactured by Thomson CSF Broadcast, Inc. At each pixel of the video frame, the television signal digitizer generates an eight bit digital signal representative of one of 256 gradations of luminance level (for a monochrome signal—as considered in the present illustrated embodiment). The video generator and the analog-to-digital converter conventionally receive synchronizing signals, and the analog-to-digital converter also receives a clock signal at the pixel rate.

The output of analog-to-digital converter 151 is coupled to a digital comparator 160 which receives as its other input another eight bit digital video signal that is output from a digital frame store 180. The output of the analog-to-digital converter 151 (i.e., the "current" digital video signal at a particular pixel) is designated as x(t), and the output of the digital frame store 180 (i.e. a stored previous minimum digital video signal at the particular pixel of the frame), is designated y(t-T), where T is the time between frames. The comparator 160 operates to generate a "0" output if the input x(t) is the lower of its two inputs, and a "1" output if the input y(t-T) is the lower of its two inputs. The output of the comparator 160 is coupled to the one input of an AND gate 171, and also to one input of another AND gate 172 via an inverter 161. The other input to AND gate 171 is the eight bit signal y(t-T) which is coupled to AND gate 171 via the delay 181. The other input to AND gate 172 is the eight bit signal x(t) which is coupled to AND gate 172 via the delay 152. The AND gates 171 and 172, when enabled by their single bit input from comparator 160 (inverted, in the case of the input to AND gate 172), pass their eight bit inputs to an OR gate 175. Since only one of the AND gates 171 or 172 can be enabled at a time, the OR gate 175 operates to pass the eight bit signal from whichever AND gate is enabled. The output of AND gate 175, designated y(t), is the current minimum digital video signal for the particular pixel of the frame being processed. This signal is stored at said particular pixel in the digital video frame store 180. The frame store 180 may comprise, for example, a model FS-963155 digital video frame store manufactured by Thomson CSF Broadcast, Inc, or, alternatively, may be any suitable memory, such as a random access memory, having pixel addresses that are synchronized with the pixel addresses of the rest of the system by driving said addresses from common sync and clock signals.

In operation of the described embodiment, a bolus of contrast material is injected into the vessel or portion of the vascular system to be imaged. Processing is then initiated. The frame store 180 is initially loaded with all zero values, so the first digitized video frame is loaded into the frame store 180. Thereafter, each sequentially digitized frame is compared, pixel-by-pixel with the corresponding pixel in the frame store 180. In particular, each pixel x(t) of the current video frame is compared with the corresponding pixel, y(t-T) from the frame store 180. The result of the comparison (by comparator 160) is used to enable either the OR gate 171 or the OR gate 172 to pass whichever luminance level is lower to the frame store 180 for restorage. The delays 152 and 181 are used to equalize processing time. Since the lowest luminance value at each pixel represents the highest opacity of the body region corresponding to the pixel, the processed image in frame store 180 is a frame of video information that represents the maximum opacity at each elemental region of the body being viewed during the time the processor is active. This processed output is preferably taken at y(t) (although y(t-T) can be used, if desired), and is coupled to display 190 and recorder 195.

Figure 2:
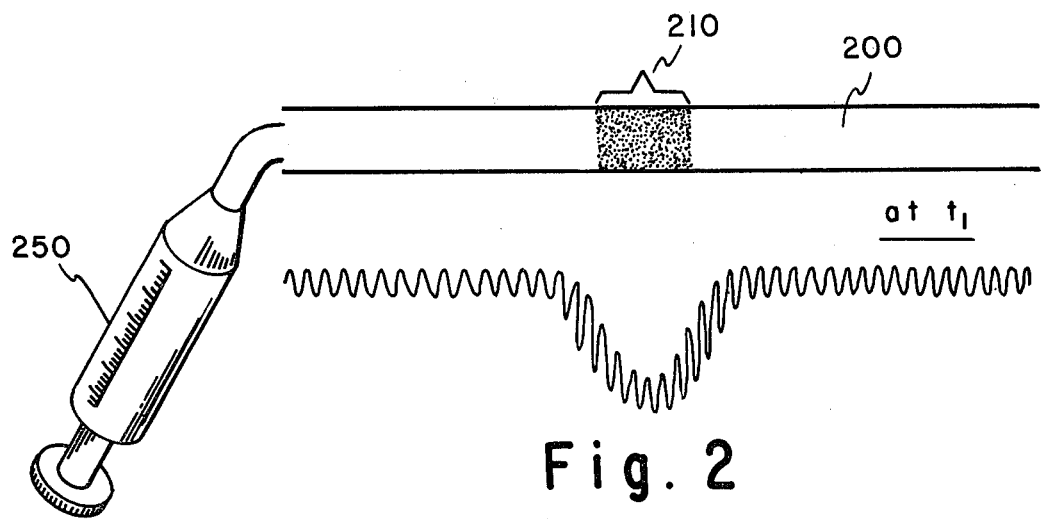
FIG. 2 illustrates the conventional imaging of a vessel without the processing of the invention.
Figure 3:
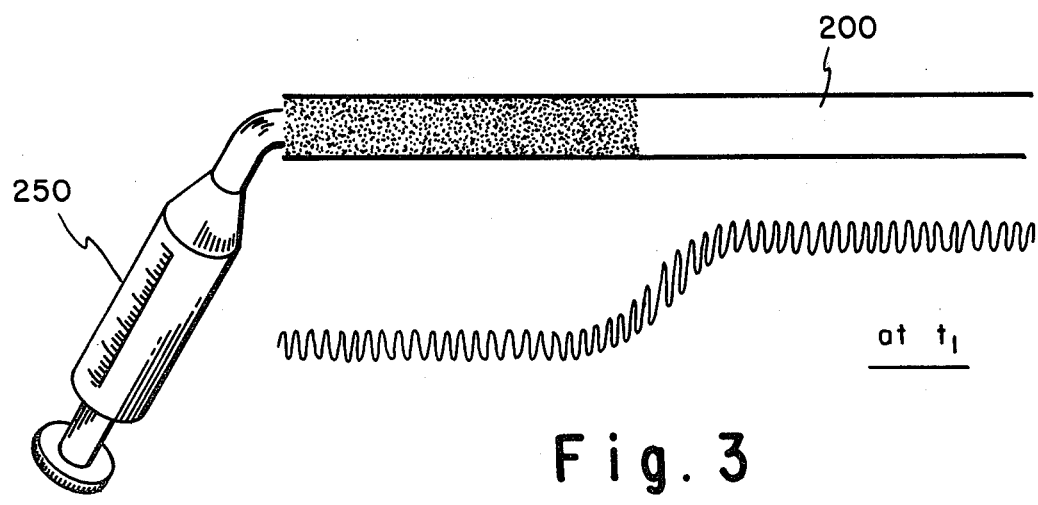
FIG. 3 illustrates the imaging of a vessel with the processing of the invention.

FIGS. 2 and 3 illustrate, in simplified terms, the image and video signal levels that are typically obtained without the processing of the present invention (FIG. 2) and with the processing of the present invention (FIG. 3). In both FIGURES, the same short bolus of contrast material is injected at a time $t_0$ into the vessel 200, as represented by the syringe 250. In FIG. 2 the bolus is shown at a time $t_1$ after injection as opacifying the portion 210 of the vessel to which the bolus has travelled. Accordingly, an unprocessed video image taken at time $t_1$ would appear as the vessel is shown in FIG. 2; i.e., with the small opacified portion of the vessel standing out clearly in the image. Below the vessel in FIG. 2 is a representation of the video signal level along the length of the vessel. The signal will typically include a certain noise level and will increase in amplitude in the region opacified by the location of the contrast material at the imaging time $t_1$.

FIG. 3 illustrates the vessel 200 as represented by the processed image at time $t_1$ in accordance with the technique hereof. Since the technique of the invention includes storing of the maximum opacification (i.e., minimum transmission) during the travel of the contrast material through the vessel, the processed image at time $t_1$ will distinctly present all portions of the vessel through which the contrast material has travelled (since the initiation of video processing), independent of when the opacification occurred. It is seen that the processed image at $t_1$ in this case presents the maximum opacification of the vessel, and thereby shows an opacified vessel up to the position the contrast material has reached by the time $t_1$. The video signal level along the length of the vessel is again shown below the vessel, and it can be noted that the amplitude range of the noise is also reduced as compared to the FIG. 2 case.

As has been demonstrated, using the technique hereof one can obtain, using a relatively short duration bolus, a processed image that is comparable to the image obtainable using a relatively long duration bolus.

I claim:

1. A method for generating a processed video image of a fluid-carrying vessel in a body, comprising the steps of:

injecting a contrast medium to pass into the vessel;
irradiating the body;
detecting radiation which passes through the body and generating a series of frames of electronic video signals that represent an image of the radiation transmission characteristics of the body at a series of different times, each frame including an array of pixels, the video signal level at each pixel being determined by the radiation transmissivity of an elemental region of the body, and operating on said series of frames as follows:
storing a frame of the sequence;
comparing the video signal level at each pixel of another frame of the sequence with the video signal level at the corresponding pixel of the stored frame;
selecting at each said pixel a video signal level representative of the lower of the compared video signal levels;
re-storing the selected video signal levels; and
displaying the selected video signal levels.

2. The method as defined by claim 1 further comprising repeating said comparing, selecting, and restoring steps with respect to further frames of the sequence which are compared to re-stored frames.

3. The method as defined by claim 2, wherein said frames of electronic video signals are frames of digitized video levels.

4. The method as defined by claim 1, wherein said frames of electronic video signals are frames of digitized video levels.

5. Apparatus for generating a processed video signal representative of an image of a body, comprising:

a source of radiation directable at the body;

means for detecting radiation which passes through the body and for generating a sequence of frames of electronic video signals that represent an image of the radiation transmission characteristics of the body, each frame including an array of pixels, the video signal level at each pixel being determined by the radiation transmissivity of an elemental region of the body;

frame storage means for initially storing a video frame of the sequence;

means for comparing the video signal level at each pixel of a different generated frame of the sequence with the video signal level at the corresponding pixel of the frame stored in said frame storage means; and means for selecting and re-storing at each said pixel a video signal level representative of the lower of the compared video signal levels.

6. Apparatus as defined by claim 5 further comprising means for displaying the video re-stored in said frame storage means.

7. Apparatus as defined by claim 6, wherein said frames of electronic video signals are frames of digitized video levels.

8. Apparatus as defined by claim 5, wherein said frames of electronic video signals are frames of digitized video levels.

9. For use in conjunction with an imaging system, including a source of radiation directable at a body; detection means for detecting radiation which passes through the body; and a display; an apparatus for generating a processed video signal representative of an image of the body; comprising:

means responsive to said detection means for generating a sequence of frames of electronic video signals that represent an image of the radiation transmission characteristics of the body, each frame including an array of pixels, the video signal level at each pixel being determined by the radiation transmissivity of an elemental region of the body;

frame storage means for initially storing a video frame of the sequence;

means for comparing the video signal level at each pixel of a different generated frame of the sequence with the video signal level at the corresponding pixel of the frame stored in said frame storage means; and means for selecting and re-storing at each said pixel a video signal level representative of the lower of the compared video signal levels.

10. Apparatus as defined by claim 9 further comprising means for displaying the video re-stored in said frame storage means.

11. Apparatus as defined by claim 10, wherein said frames of electronic video signals are frames of digitized video levels.

12. Apparatus as defined by claim 9, wherein said frames of electronic video signals are frames of digitized video levels.

* * * * *